United States Patent [19]

Gindler

[11] 4,246,133

[45] Jan. 20, 1981

[54] STABILIZED DIAZOTIZED SULFANILIC ACID SOLUTIONS

[75] Inventor: E. Melvin Gindler, Rockford, Ill.

[73] Assignee: Sherwood Medical Industries Inc., St. Louis, Mo.

[21] Appl. No.: 51,228

[22] Filed: Jun. 22, 1979

Related U.S. Application Data

[63] Continuation of Ser. No. 765,961, Feb. 7, 1977, abandoned.

[51] Int. Cl.³ .............................................. C09K 3/00
[52] U.S. Cl. .................................. 252/408; 23/230 B
[58] Field of Search .......... 252/408; 23/230 B, 230 R

[56] References Cited

U.S. PATENT DOCUMENTS

| | | | |
|---|---|---|---|
| 3,853,466 | 12/1974 | Rittersdorf et al. | 252/408 X |
| 3,853,476 | 12/1974 | Rittersdorf et al. | 23/253 TP |
| 3,880,588 | 4/1975 | Rittersdorf et al. | 252/253 TP |
| 4,038,031 | 7/1977 | Lam | 252/408 |
| 4,078,892 | 3/1978 | Steinbrink | 252/408 |

*Primary Examiner*—Benjamin R. Padgett
*Assistant Examiner*—J. L. Barr
*Attorney, Agent, or Firm*—Wegner, Stellman, McCord, Wood & Dalton

[57] ABSTRACT

Nitrilotris (methylene) triphosphonic acid and 1,3,6-napthalenetrisulfonic acid are used to stabilize solutions containing diazotized sulfanilic acid.

1 Claim, No Drawings

STABILIZED DIAZOTIZED SULFANILIC ACID SOLUTIONS

This is a continuation of application Ser. No. 765,561, filed Feb. 7, 1977, now abandoned.

The present invention relates to the stabilization of diazotized sulfanilic acid.

In the well known Jendrassik and Grof procedure for the determination of bilirubin, an azobilirubin complex is formed, the color intensity of which is then measured either colorimetrically or spectrophotometrically. As conventionally practiced, formation of the azobilirubin complex is effected by reacting bilirubin with diazotized sulfanilic acid, a p-sulfophenyldiazonium salt, in dilute HCl. The diazonium salt is prepared by reacting sodium nitrite with sulfanilic acid and, because the salt is recognized as being unstable, it is necessary to prepare the salt immediately to a day or two days before use.

An object of the present invention resides in providing a manner in which the diazonium salt can be stabilized such that, after preparation, it can be stored; thus obivating the necessity for immediate use.

To this end, it has been found that by including the combination of nitrilotris (methylene) triphosphonic acid and 1,3,6-napthalenetrisulfonic acid in the solution containing the diazonium salt, the solution is stable for at least two days at room temperature and about three months when refrigerated.

EXAMPLE

The following solutions are prepared:

Sulfanilic Acid Reagent

One liter of this solution is deionized water contains:
5.0 grams (26.15 mMol) p-sulfanilic acid monohydrate
60 ml (720 mMol) 12M (conc.) HCl
5 ml 50% nitrilotris (methylene) triphosphonic acid
15 gm 1,3,6-napthalenetrisulfonic acid trisodium salt

Sodium Nitrite Solution

One hundred milliliters of this solution is deionized water contains:
20.0 grams (0.2898 Mol) $NaNO_2$
0.090 grams tetrasodium salt of ethylenediaminetetraacetic acid, dihydrate A solution of the present invention, useful in the determination of bilirubin, is then prepared by mixing 250 volumes of the sulfanilic acid reagent with 1 volume of the sodium nitrite reagent. The color reagent, so prepared, is remarkably stable.

I claim:

1. In a solution containing diazotized sulfanilic acid, the improvement wherein the solution also contains nitrilotris (methylene)-triphosphonic acid and 1,3,6-napthalenetrisulfonic acid in an amount which serves to stabilize said solution.

* * * * *